United States Patent
Koo et al.

[11] Patent Number: 5,846,203
[45] Date of Patent: Dec. 8, 1998

[54] METHOD AND APPARATUS FOR NOISE SUPPRESSION IN A DOPPLER ULTRASOUND SYSTEM.

[75] Inventors: Ja-Il Koo, Phoenix, Ariz.; Dong-Chyuan Liu, Mercer Island, Wash.

[73] Assignee: Siemens Medical Systems, Inc., Iselin, N.J.

[21] Appl. No.: 827,283

[22] Filed: Mar. 27, 1997

[51] Int. Cl.⁶ .................................................... A61B 8/00
[52] U.S. Cl. ........................................... 600/454; 600/447
[58] Field of Search ...................... 128/661.08; 364/574

[56] References Cited

U.S. PATENT DOCUMENTS

| | | | |
|---|---|---|---|
| 5,349,524 | 9/1994 | Daft et al. | 128/661.08 |
| 5,357,965 | 10/1994 | Hall et al. | 128/661.08 |
| 5,409,007 | 4/1995 | Saunders et al. | 128/661.08 |
| 5,445,156 | 8/1995 | Daft et al. | 128/661.08 |
| 5,503,153 | 4/1996 | Liu et al. | 128/661.08 |
| 5,647,366 | 7/1997 | Weng | 128/661.08 |

*Primary Examiner*—Marvin M. Lateef
*Assistant Examiner*—Maulin Patel

[57] ABSTRACT

Ultrasound echo data is analyzed to compress jump noises by recalculating the value of data points whose magnitude exceeds the magnitude of a previous point by more than a predefined threshold. Any data that exceeds the threshold is recalculated according to the value of the slopes of the points that precede and after the point to be replaced. The value by which a data point is compressed is selected so that the DC component of the points after compression is nearly equal to the DC component of the points prior to the jump noise. In addition, to remove saturating clutter in a Doppler display or audio signal, the present invention determines if the power spectrum of the Doppler signals to be displayed exceeds a maximum power display and if so scales a portion of the I and Q signals that comprise the Doppler power spectrum by the ratio of the maximum power spectrum computed and the maximum that can be displayed.

10 Claims, 4 Drawing Sheets

METHOD AND APPARATUS FOR NOISE SUPPRESSION IN A DOPPLER ULTRASOUND SYSTEM.

FIELD OF THE INVENTION

The present invention relates to ultrasound systems in general, and in particular to noise suppression in Doppler ultrasound systems.

BACKGROUND OF THE INVENTION

Ultrasound is becoming an increasingly used method of noninvasively examining the interior body matter of a patient. Ultrasound systems work by transmitting high frequency acoustic energy into a region of interest and detecting and analyzing the reflected echoes signals. Most ultrasound systems provide a physician or sonographer with an image of the regional interest under examination. In addition, many ultrasound systems also provide the physician or sonographer with Doppler information that is indicative of the velocity or movement of the tissue or blood in the region of interest. The Doppler information is often displayed as an image of the velocity or frequency of the blood flow versus time. In addition, the Doppler information is often conveyed as an audio signal so that a physician or sonographer can hear the blood flow.

In any ultrasound system, the quality of the Doppler image or audio signal produced is directly affected by the noise level of the received echo signals and in the processing electronics. Noise in the processing electronics can occur from such sources as a user changing the receiver gain of the ultrasound Doppler system or from random noise that occurs in the semiconductor components of the ultrasound system. Noise in the received echo signals can also occur due to large movements of arterial or muscle walls within the region of interest. These types of noise, which are typically characterized by large changes in signal amplitude, are generally referred to as "jump noise" due to the signal discontinuity.

Each source of jump noise described above tends to degrade the corresponding ultrasound display and audio in a characteristic fashion. For example, random electronic noise contains wideband frequency components that produce strong vertical lines in a Doppler ultrasound image. Noise created by big movements in arterial or muscle walls or changes in the settings of the ultrasound system tends to create big amplitude wideband frequency clutter or bright spots that appear in a Doppler ultrasound image mainly due to the signal saturation. In the Doppler audio signal, the jump noise creates distracting clicks or pops.

In the past, ultrasound systems have used digital wall filters to reduce or eliminate the effects of jump noise in a corresponding Doppler image or audio signal. However, due to the low cutoff frequency and steep skirts required of the wall filter, such filters tend to be computationally complex, are sometimes unstable, and are often unable to fully remove the artifacts created by the noise. Therefore, there is a need for an ultrasound system that can better reduce the effects of jump noise in the ultrasound system without requiring complex wall filters.

SUMMARY OF THE INVENTION

To reduce the effects of jump noises in a Doppler image and audio signal, the present invention comprises a system for processing ultrasound echo data to remove wideband frequency noise and saturating clutter. An ultrasound system that operates according to the present invention analyzes sets of ultrasound data. The magnitude of each data point in the set is compared with the magnitude of a previous point to determine if the data jumps by more than a predetermined threshold. If so, the value of the points that exceed the predetermined threshold are compressed by calculating a new value that is dependent upon the magnitude of the previous data point and the slopes of the points that precede and are after the point to be replaced.

If the slope of the points that are after the point in question do not exceed a predetermined threshold, then the new magnitude for the point in question is calculated by subtracting a scaling value equal to the difference in magnitude between the point in question and the previous point less the average of the slopes that precede and are after the point in question. This scaling value is stored and subtracted from subsequent points in the data set until the magnitude of two sequential points exceeds the threshold whereupon the scaling value is updated.

If the slope of the points after the point in question exceeds a predetermined threshold, then the scaling value subtracted from the point in question is calculated by subtracting the difference in magnitude between the point in question and the previous point less the value of the slope of the points preceding the point in question if the slopes before and after the point in question have the same direction. Alternatively, if the slopes of the points before and after the point in question have opposite signs, the scaling value is calculated by subtracting the difference in magnitude between the point in question and the previous point less the inverse of the slope of the points preceding the point in question.

To eliminate the effects of saturating clutter in the Doppler signals, the power spectrum of the Doppler ultrasound signal is computed. The power spectrum is compared with a maximum power spectrum that can be displayed by the ultrasound system. If the power spectrum computed exceeds the maximum power spectrum that can be displayed, then a portion of the I and Q components that comprise the spectrum are scaled by the ratio of the maximum computed power spectrum and the maximum power spectrum that can be displayed. The portion of I and Q signals that are scaled is determined as a fraction of the maximum power spectrum.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENT

The present invention is a method for reducing the effects of jump noise in a Doppler ultrasound system. As will be described in further detail below, the present invention operates to compress large variations in the received Doppler signals in a way that does not effect the high frequency information contained in the Doppler signals.

Figure 1:
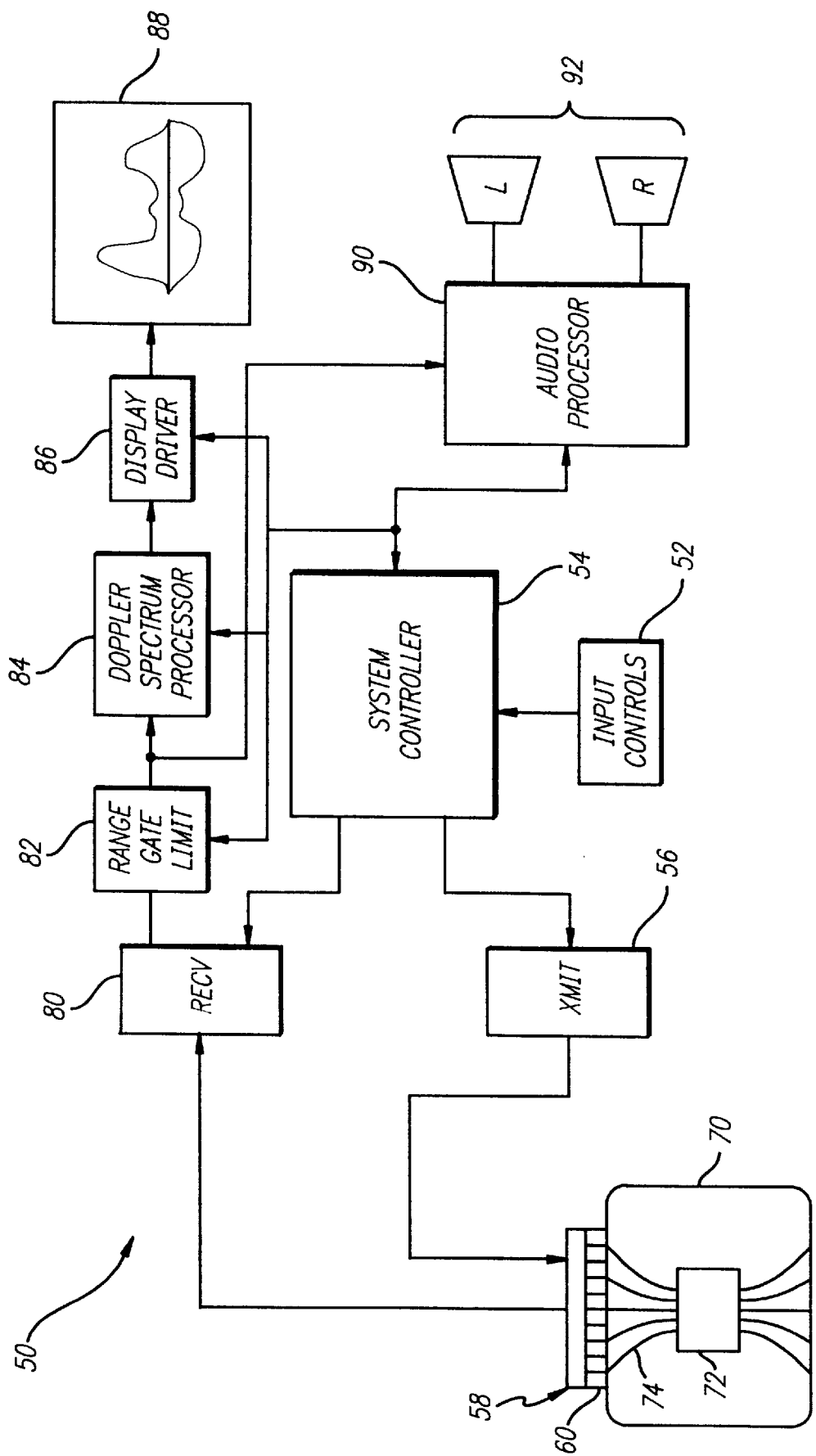
FIG. 1 is a block diagram of a Doppler ultrasound system in which the present invention is incorporated.

FIG. 1 illustrates a basic block diagram of an ultrasound system of the type in which the present invention is utilized. The ultrasound system 50 includes a set of input controls 52, such as a keyboard, knobs and buttons, on which a user enters conventional scan parameters. The input control 52 is electrically connected to a system controller 54 that typically includes one or more electrically connected and cooperating microprocessors and digital signal processors.

The system controller 54 sets, adjusts and monitors the operation parameters of a transmission control unit 56. The transmission control unit 56 generates and applies electrical control and driving signals to an ultrasonic probe 58 that include an array of piezoelectric elements 60. The piezoelectric elements generate ultrasonic sound waves when driving signals of the proper frequency are applied to them.

By placing the probe 58 against the body 70 of a patient, the ultrasonic sound waves enter an interrogation region 72 of the patient's body. By varying the amplitude and time of the driving signals applied to the individual piezoelectric elements 60, the ultrasonic waves are focused along a series of scan lines 74 that typically fan out from the probe.

In most common applications of ultrasonic scanning, the interrogation region 72 is scanned as a pattern of 2-D planes in order to generate 2-D information, such as a spatial map of the intensity of the returned echo signals from the interrogation region, or a 2-D map of the velocity of the tissue or blood flow moving within the region. Other techniques using both 1-D and 2-D arrays are known that allow scan beams to lie in different planes and thus generate 3-D representations of the scanned region and to sense blood flow with three independent velocity components. The manner in which the ultrasonic signals are controlled, generated and applied to the patient's body are well known to those of ordinary skill in the ultrasound arts and need not be described in further detail below except as they relate to the present invention.

Ultrasonic echoes from the sound waves transmitted into the body return to the array of piezoelectric elements 60 of the probe 58. The piezoelectric elements convert the small mechanical vibrations caused by the echoes into corresponding radio-frequency (RF) electrical signals. Amplification and other conventional signal conditioning is then applied to the returned signals by a receiver 80. Typically, the returned signals are digitized, delayed, and combined, in order to form a sequence of data representing the strength of the echoes that occur at a number of points along a scan line 74.

The data produced by the receiver 80 is applied to a range gate limiter 82 that defines a window in which samples will be used to compute the Doppler shift. The output of the range gate limiter feeds a Doppler spectrum processor 84 that filters the data and computes the Doppler shifts. The output of the Doppler spectrum processor 84 feeds a display driver 86 that operates in conjunction with the monitor 88 to produce a graph of the velocity or frequency of the tissue or blood flow in the interrogation region versus time.

In addition to the Doppler spectrum processor and display driver that produce images of the interrogation region, the ultrasound system also includes an audio processor 90. The audio processor receives the range-gated Doppler data from the range gate limiter 82, performs proper operations to get right and left speakers' Doppler digital information and converts the digital information to a suitable analog form, and drives a pair of speakers 92. One speaker produces sounds representative of blood or tissue moving away from the ultrasonic probe 58, while the other speaker produces signals representative of blood or tissue moving toward the probe.

Figure 2A:
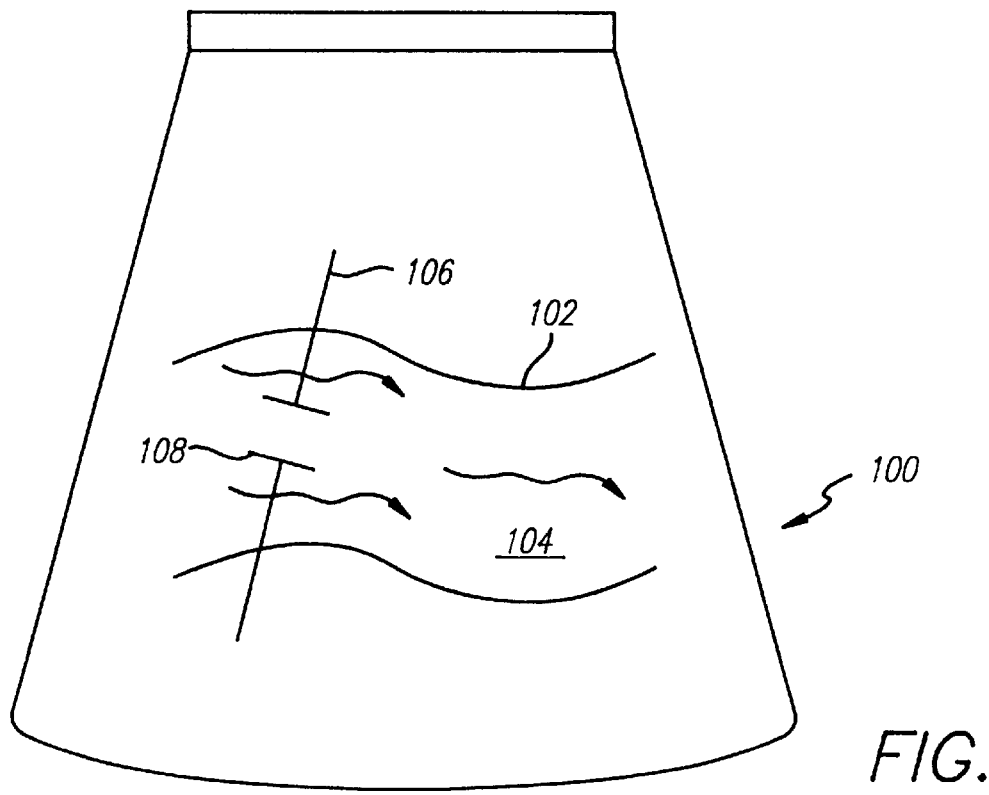
FIG. 2A illustrates a conventional ultrasound image superimposed with range gate.

FIG. 2A illustrates a conventional image with range gate, which is produced by the ultrasound system shown in FIG. 1. The ultrasound image 100 is typically a fan-shaped display of the tissue that is positioned under the ultrasonic probe. In the example shown in FIG. 2A, the display illustrates an artery 102 having an amount of blood 104 flowing through it. If the ultrasound system is operated in a Doppler mode, a range gate 106 is superimposed on the ultrasound image. The user can then position a pair of parallel-spaced lines 108 of the range gate at some point within the ultrasound image. The position of the parallel lines serves to define the depth from which the returned echo signals are analyzed to create the Doppler information.

Figure 2B:
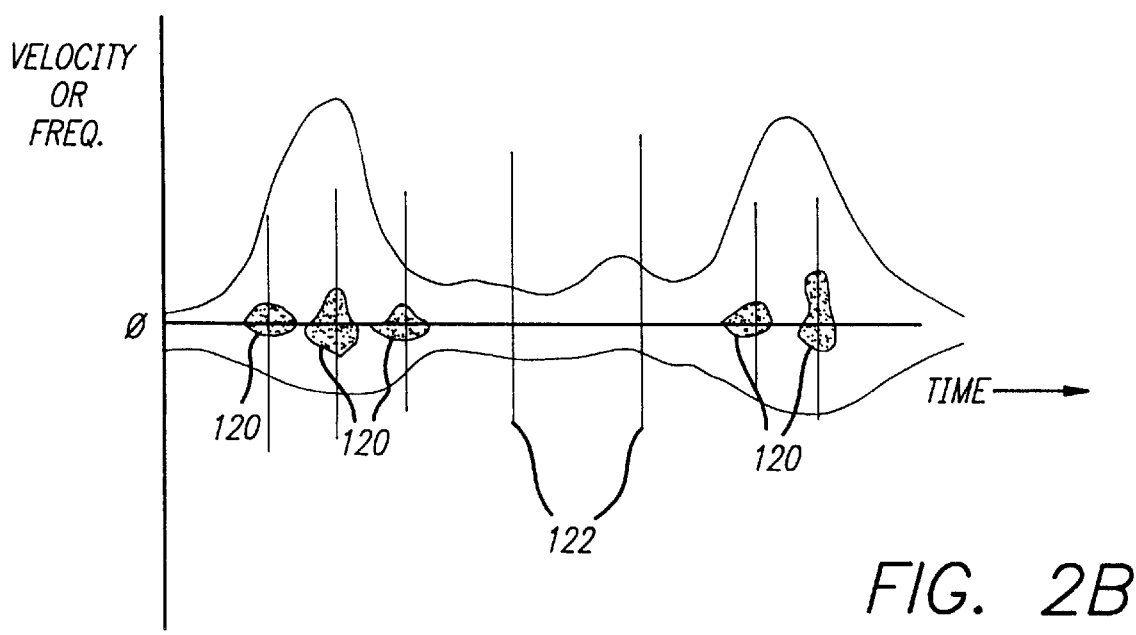
FIG. 2B illustrates a Doppler ultrasound image with artifacts caused by jump noise.

FIG. 2B illustrates a typical Doppler ultrasound display. The display illustrates the velocity of the moving tissue or blood flow at the depth specified by the position of the range gate. As indicated above, the Doppler display is susceptible to various types of jump noise that degrade the image. One type of noise occurs when a user changes the settings of the ultrasound system as it is operating. For example, the user may change the gain of the receiver circuitry. Alternatively, the user may position the range gate over the wall of an artery or adjacent a muscle that moves as the Doppler image is being created. Both events tend to produce wideband frequency noise due to sign discontinuity, large amplitude signals that appear as bright clutter spots 120 in the Doppler image. These clutter spots impair the ability of the physician or sonographer to analyze the slowly moving blood or tissue.

In addition, the ultrasound system is subject to random noise spikes in the receiver circuitry. These randomly occurring spikes contain many low and high frequency components and tend to appear as faint vertical lines 122 in the Doppler display.

While it is possible to remove some of the wideband clutter spots 120 from the image using a specialized wall filter, such filters tend to be computationally complex and can be unstable. In addition, wall filters have not been successful in removing all the artifacts created by jump noise.

To reduce the effects of jump noises, the present invention analyzes the ultrasound echo data as it is received in real time and compresses any peaks that exceed a predefined limit while preserving the Doppler information contained in the data. This pre-processing is done before the data is applied to a conventional wall filter.

The ultrasound system processes the echo data in sets that are received at a certain period of time. The number of echo data is typically determined by several system parameters, such as Doppler PRF vertical sync rate. The jump noise pre-processing compression algorithm of the present invention compares the magnitude of sequential points in the data set and determines whether that difference exceeds a predetermined threshold $\delta$. If the difference in magnitude exceeds the threshold, the slope of the points prior to and after the point in question are determined. To determine the slope of the points preceding the point in question, the compressed or recalculated data points (if applicable) are used. If the slopes of the points after the point in question to not exceed the threshold δ, then the value of the point in question is recalculated by subtracting a scaling value equal to the difference in magnitude between the point in question and the point immediately preceding less the average slopes of the points preceding and after the point in question.

If the slope of the points after the point in question does exceed the threshold δ, then the value of the point in question is recalculated by subtracting a scaling value equal to the difference between the point in question and the point immediately preceding less the value of the slope for the points preceding the point in question (if the slopes before and after the point in question are in the same direction), or less the inverse of the slope of the previous points (if the slopes of the points before and after the point in question have different directions).

The value of the scaling value will remain the same until another pair of sequential points differs by more than the predetermined threshold δ. At this time, the old scaling value is added to the new scaling value. As will be described below, the scaling value ensures that the DC value of the points before the jump noise remains substantially the same as the DC value of the points after the removal of the jump noise.

The pre-processing compression algorithm described above does not distort the original information of the Doppler signal because it ensures that the first derivative of the Doppler data changes smoothly between adjacent data points. The slope of the points after compression can at most change between a range defined by the slope of the points preceding the point in question and the slope of the points after the point in question.

The following pseudo code illustrates how the pre-processing algorithm described above is actually implemented in a digital signal processor within the ultrasound system. The ultrasound echo data is loaded into a buffer containing the sample $h_0, h_1, h_2 \ldots h_{n-1}$ that are indexed by the variable j. The points $h_1$ through $h_{n-3}$, are analyzed in the following manner:

```
do {
    load δ(G) as a function of the user selectable digital gains.
    if (|h_j - h_{j-1}| > δ(G)) {/* jump noise */
        slopehd j-1 = h'_{j-1} - h'_{j-2};
        slope_{j+1} = h_{j+2} - h_{j+1};
        if (|slope_{j+1}| > δ(G)){/* jump noise again */
            if(sgn(slope_{j-1}) × sgn(slope_{j+1}) = -1)
                η_j = -slope_{j-1};   /* change slope
direction */
            else
                η_j = slope_{j-1};
            }
        else
            η_j = ½ (slope_{j-1} + slope_{j+1});    /* linear
interpolation */
        H = h_j - h_{j-1} + H - η_j
        h'_j = h_j - H;
    j = j + 1;
} while (not end of buffer);
``` where the scaling value H equals zero and j equals 1 upon initialization.

Special steps are taken for the first data point in the buffer wherein the slopes are analyzed as follows:

```
h'_0 = h_0
slope_0 = h_1 - h_0
if (|slope_0| > δ(G)) {
    η_0 = h_3 - h_2
    H = H ++slope_0 - η_0
    }
h'_1 = h_1 - H.
```

Similarly the last two data points, $h_{n-2}$ and $h_{n-1}$ are analyzed as follows:

```
slope_{n-2} = h_{n-2} - h_{n-3}
if (|slope_{n-2}| > δ(G)) }
    η_{n-2} = h'_{n-3} - h'_{n-4}
    H = H + slope_{n-2} - η_{n-2}
    }
h'_{n-2} = h_{n-2} - H
h'_{n-1} = h_{n-1} - H.
```

The threshold δ(G) is a function of the user selectable gain of the ultrasound system. If δ is made too small, then the pre-processing algorithm set forth above will remove too many of the high frequency components of the ultrasound echo data. Conversely, if δ is made too large, then the algorithm will not be effective in compensating for the jump noises. In the presently preferred embodiment of the invention, the relationship between δ and the user selectable gain is defined, in a look up table, wherein the value of δ for each gain setting is empirically determined using test data and the particular ultrasound system to remove the jump noise.

Figure 3A:
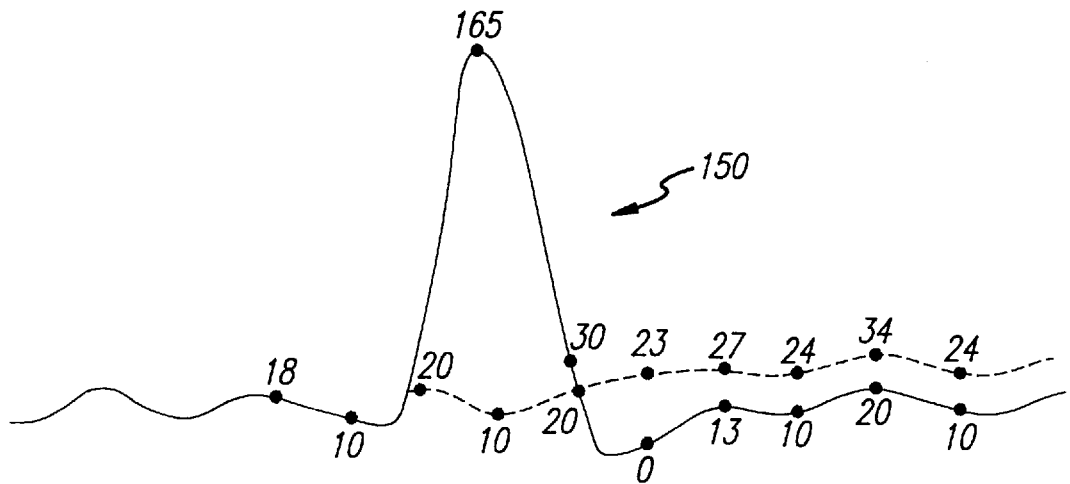
FIG. 3A illustrates how spurious jump noise is attenuated according to the method of the present invention.

FIG. 3A illustrates how the method of the present invention operates to suppress a randomly occurring jump noise in the set of ultrasound echo data. The following table contains the values of the echo data points shown prior to and after compression.

TABLE 1

| (δ = 10) | | | | | | | | | | |
|---|---|---|---|---|---|---|---|---|---|---|
| Prefiltering | 18 | 10 | 20 | 165 | 30 | 0 | 13 | 10 | 20 | 10 |
| Post Filtering | 18 | 10 | 20 | 10 | 20 | 23 | 27 | 24 | 34 | 24 |

The unfiltered data is shown as the solid line graph in FIG. 3A and contains a spike of 165 at the fourth data point and other non-normal points 30, 0, and 13, because the data values vary by more than the δ value. The operation of the present invention serves to attenuate this spike to 10, and proceeds to update the subsequent values as indicated by the dotted line. The effect of the algorithm set forth above is to reduce any large spikes or jump noises in the raw echo data without affecting the high frequency components contained therein. As can be seen, the dotted line tracks the original signal with a constant offset determined by the value of the scaling constant, H. This is equivalent to adding a small DC component to the input signal which can be easily removed with a simple wall filter.

Figure 3C:
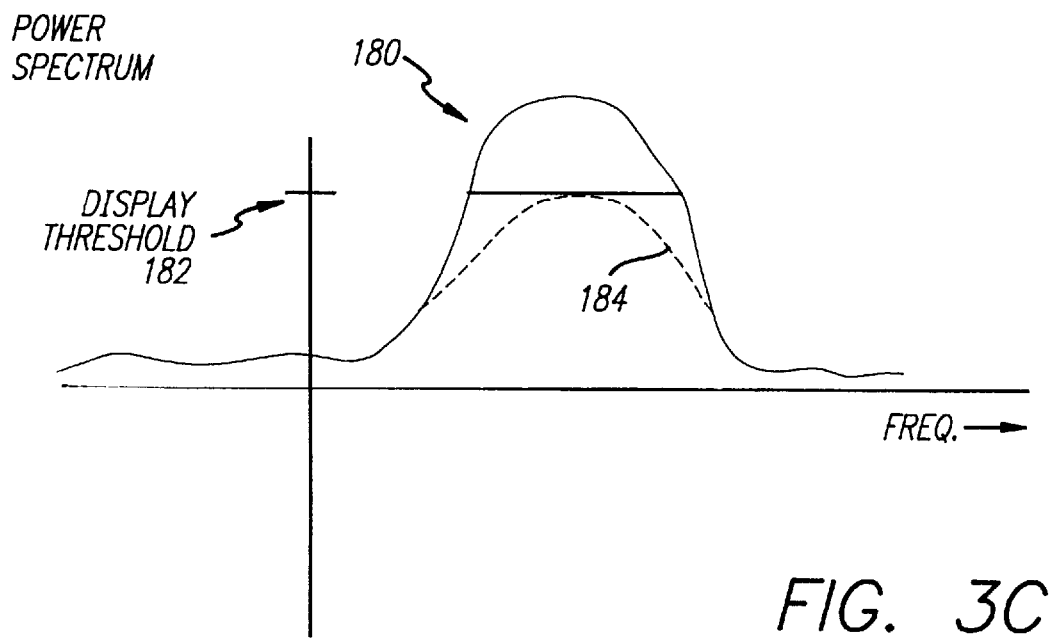
FIG. 3C illustrates how Doppler signals exceeding a display threshold are compressed according to the present invention.
Figure 3B:
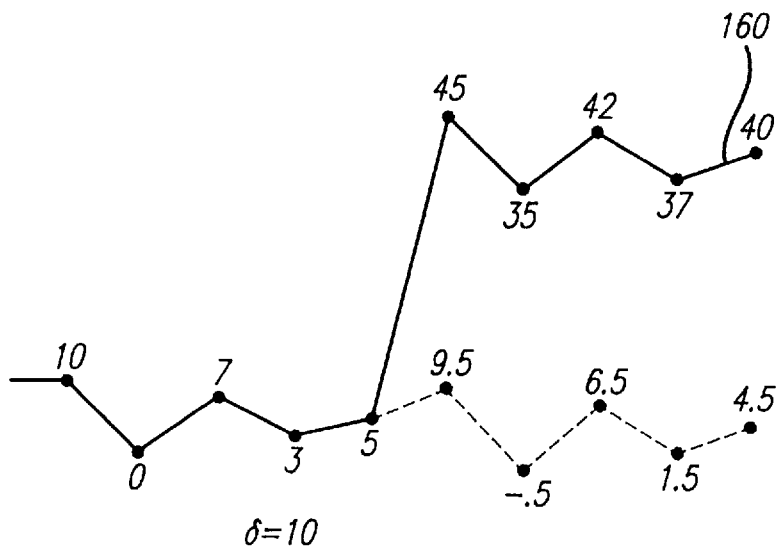
FIG. 3B illustrates how the present invention eliminates jump noise if the level of an ultrasound signal changes due to the gain change.

FIG. 3B illustrates how the invention reduces jump noise that may occur as a result of a user changing the gain of the receive circuitry. The following table shows the values of the echo data prior to and after the jump noise suppression algorithm.

TABLE 2

| (δ = 10) | | | | | | | | | |
|---|---|---|---|---|---|---|---|---|---|
| Prefiltering | 10 | 0 | 7 | 3 | 5 | 45 | 35 | 42 | 37 | 40 |
| Post Filtering | 10 | 0 | 7 | 3 | 5 | 9.5 | -0.5 | 6.5 | 1.5 | 4.5 |

The original data 160 is shown as the solid line while the compressed or updated data is shown as the dotted line. As can be seen, the DC value of the echo data is increased at the sixth data point where it jumps from a value of 5 to a value of 45. Thereafter, the data has a DC component value of approximately 40. The present invention reduces the magnitude of all the data points after the jump point so that the DC component of the recalculated points is substantially equal to the DC component value prior to the jump point. This is accomplished by the scaling value H described above.

As indicated above, another problem that occurs with conventional Doppler ultrasound systems is that wideband frequency clutter can saturate the display. Attempts to simply reduce the intensity of a portion of the Doppler display will also remove the high frequency components that are of interest to the physician or sonographer.

To correct for the saturating clutter signals, the present invention reduces the intensity of these signal by first filtering the echo data that has been compressed according to the pre-processing method described above with a simple wall filter. Next, the spectrum $V_s$ and its in phase and quatrature components, $H_I$ and $H_Q$ are computed using a conventional fast Fourier transform (FFT). From the in phase and quatrature components of the spectrum, the power spectrum of the Doppler signal is computed and the peak of the power spectrum is designated $V^*_s$. If $V^*_s$ is greater than $H_{max}$ where the $H_{max}$ is the largest spectral power that can be displayed on the monitor, then the following scaling is performed.

$$H_{I/Q}(i) = \begin{cases} H_{I/Q}(i) \times \frac{H_{max}}{V^*_s} & \text{if } V_s(i) > V_s^c \\ H_{I/Q}(i) & \text{otherwise} \end{cases}$$

where $V_s^c$ is a fraction, c, of the maximum power spectrum $V^*_s$. In the presently preferred embodiment of the invention, the fraction, c, is set to 0.1 to provide 20 dB of compression in order to maintain the high-frequency components of the echo data.

After the echo data is compressed in the frequency domain, the echo data is converted back into the time domain by applying an inverse fast Fourier transform (FFT$^{-1}$). Any DC components of the restored signals are then removed by subtracting the mean value of the echo data (both the I and Q components). Next, the time domain echo data are scaled with by ratio $h_{max}/h_{greatest}$ where $h_{max}$ is the largest Doppler data that can be displayed (i.e., 255 for an 8 bit system) and $h_{greatest}$ is the largest h value data point after scaling as described above. Finally, the beginning and end points of the time domain signals are smoothed with a low-pass box filter to remove any discontinuities that occur as a result of the scaling.

The conversion of the scaled I and Q frequency domain signals back to the time domain is only needed if the ultrasound system produces audio Doppler signals. The audio processor 90 shown in FIG. 1, receives the scaled, time domain echo data and produces audio signals in the left and right speakers 92 that are representative of the forward and reverse blood flow. If the ultrasound system only produces a Doppler image on the display, it is not necessary that the scaled I and Q frequency domain echo data be converted back to the time domain with the FFT$^{-1}$ algorithm. Instead, the scaled I and Q echo data are used to produce the Doppler image directly.

FIG. 3C illustrates how the present invention removes saturating clutter spots from a Doppler image and saturating audio from an audio Doppler signal. A power spectrum 180 computed from the I and Q components of the Doppler signals exceeds a threshold 182 that can be displayed on the ultrasound system's display screen. Most currently available displays have 8 bits of intensity resolution. Therefore the threshold 182 is set to be whatever Doppler intensity equates to the maximum that can be displayed with the particular display device used by the ultrasound system. After determining that the maximum power spectrum exceeds the threshold 182, each point in the power spectrum is compared to a fraction of the maximum spectrum. If the point in the power spectrum exceeds the fraction, the I and Q components that define the point are scaled in the manner described above. The result is that the power spectrum will fit within the threshold as indicated by the dotted line 184.

The post-filtering compression algorithm described above does not distort the low power frequency components of the Doppler signal because only the frequency components that surrounds the peak Doppler power is modified. The level of power that are compressed is adjustable with the size of the fraction c described above.

Figure 4:
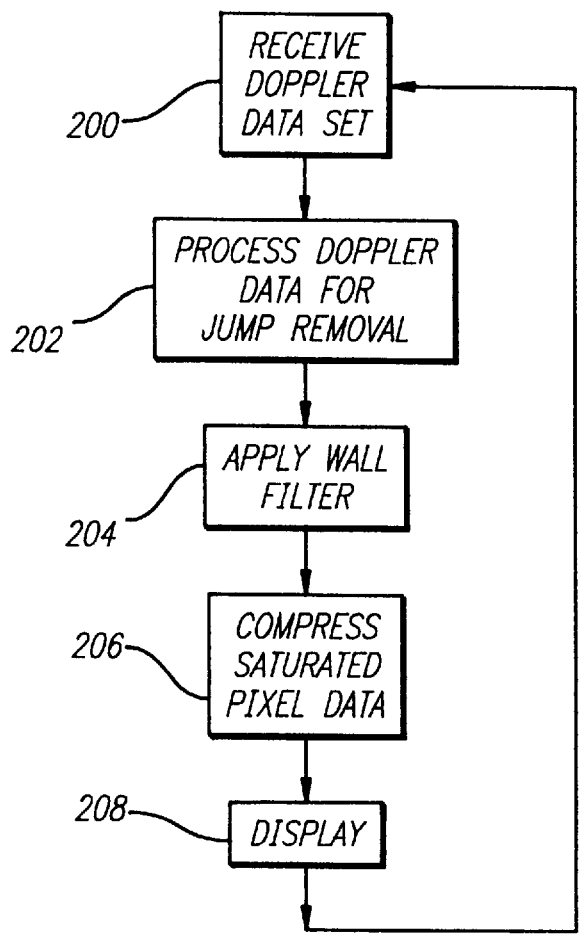
FIG. 4 is a flow chart illustrating the steps performed by the ultrasound system according to the present invention to reduce the effects of jump noise.

FIG. 4 is a flow chart of the method of processing ultrasound data according to the present invention. Beginning at a step 200, the ultrasound system receives a set of ultrasound echo data received on one beam line during a certain period of time. At a step 202, the echo data is to remove jump noise, according to the pre-processing algorithm described above. At a step 204, a conventional wall filter is applied to the pre-processed echo data processed at step 202. The conventional wall filter may be, for example, a step initialized second order IIR digital filter that is cascaded to provide the appropriately step skirts and cutoff frequency. The design of such wall filters is considered well known to those of ordinary skill in the digital signal processing arts At a step 206, the filtered echo data is then analyzed to determine whether the power spectrum of the Doppler signals exceeds the allowable limits that can be displayed. If so, then the echo data is scaled to fit with the allowable limits according to the post-processing as described above. The Doppler image and audio signals are then produced at a step 208, and the process repeats.

As can be seen from the above description, the present invention operates to reduce the effects of jump noise and signal saturation in a Doppler ultrasound system without the use of complex or potentially unstable wall filters. The algorithm is efficient enough to be run in real time without requiring significant additional processing power.

The embodiments of the invention in which an exclusive property or privilege is claimed are defined as follows:

1. A method of operating an ultrasound system to remove jump noise from a received ultrasound signal, comprising:
   digitizing the received ultrasound signal to create a set of ultrasound echo data points;
   analyzing the set of ultrasound echo data points for sequential echo data points having a difference in value that exceeds a predetermined threshold; and
   calculating a new value for those sequential data points that have values that change by more than the predetermined threshold, wherein the new values for the sequential echo data points are selected so that a DC component of the sequential echo data points that are recalculated is substantially equal to a DC component of the echo data points that are prior to the recalculated data points.

2. The method of claim 1, wherein the step of calculating the new values for the sequential echo data points have values that change by more than the predetermined threshold further comprises:

finding a point in question in the set of ultrasound echo data points whose value exceeds the value of a preceding echo data point by more than the predetermined threshold;

determining a slope for the echo data points in the set of ultrasound echo data points that precede and are after the point in question;

determining if the slope for the echo data points after the point in question exceeds the predetermined threshold and if not, computing an average slope of the echo data points that precede and are after the point in question; and subtracting from the point in question a scaling value substantially equal to the difference in value between the point in question and the value of the preceding echo data point less the average slope.

3. The method of claim 2, further comprising:

determining if the slope of the echo data points after the point in question exceeds the predetermined threshold; and determining if the slope of the echo data points preceding the point in question and the slope of the echo data points after the point in question have the same direction;

wherein the scaling value subtracted from the point in question has a value substantially equal to the difference in value between the point in question and the preceding echo data point less the slope of the echo data points that precede the point in question if the slope of the echo data points preceding the point in question and after the point in question have the same direction.

4. The method of claim 3, wherein the scaling value subtracted from the point in question has a value that is substantially equal to the difference in value between the point in question and the preceding echo data point less an inverse of the slope of the echo data points that precede the point in question if the slope of the echo data points that precede the point in question and the slope of the echo data points that are after the point in question are in different directions.

5. The method of claim 2, further comprising calculating a new value for each echo data point after the point in question by subtracting the scaling value from each echo data point.

6. The method of claim 5, further comprising updating the scaling value each time a number of sequential echo data points in the set of echo data points have a difference in value that exceeds the predetermined threshold.

7. The method of claim 1, further comprising:

filtering the set of ultrasound echo data points with a wall filter;

computing from the filtered set of echo data points an in-phase (I) and quadrature (Q) Doppler signal and computing a Doppler power spectrum from the I and Q Doppler signals; and determining if any points in the Doppler power spectrum exceed a maximum power spectrum that can be displayed by the ultrasound system, and if so, scaling a portion of the I and Q Doppler signals such that the power spectrum does not exceed the maximum Doppler power spectrum that can be displayed.

8. The method of claim 7, wherein the step of scaling a portion of the I and Q Doppler signals further comprise:

determining if the I and Q Doppler signals exceed a fraction of a peak in the Doppler power spectrum, and if so, scaling the I and Q Doppler signals by a ratio of the peak Doppler power spectrum and the maximum Doppler power spectrum that can be displayed by the ultrasound system.

9. An ultrasound system, comprising:

an ultrasonic probe that transmits and receives ultrasound signals into a patient;

a receiver coupled to the ultrasonic probe that receives echo signals from the patient and produces a set of ultrasound echo data points that represent the received echo signals;

a pre-processor that filters the ultrasound echo data points to reduce any jump noises by recalculating values for those ultrasound echo data points having a value that differs from a previous ultrasound echo data point by more than a predetermined amount, wherein the values for the recalculated ultrasound echo data points are determined by subtracting a scaling value from the ultrasound echo data points so that a DC component of the ultrasound echo data points that have been recalculated is substantially the same as the DC component for those ultrasound echo data points that precede the ultrasound echo data points that are recalculated.

10. The ultrasound system of claim 9, further comprising:

a wall filter that filters the ultrasound echo data points to remove any DC component;

a post-processor that compresses the wall filtered ultrasound echo data points to ensure that a Doppler signal produced from wall filtered the ultrasound echo data points does not exceed a display threshold.

* * * * *